US009737229B1

(12) United States Patent
Gupta et al.

(10) Patent No.: US 9,737,229 B1
(45) Date of Patent: Aug. 22, 2017

(54) NONINVASIVE ELECTROCARDIOGRAPHIC METHOD FOR ESTIMATING MAMMALIAN CARDIAC CHAMBER SIZE AND MECHANICAL FUNCTION

(71) Applicant: Analytics For Life, Kingston (CA)

(72) Inventors: Sunny Gupta, Amherstview (CA); Derek Exner, Calgary (CA); Mohsen Najafi Yazdi, Kingston (CA); Timothy William Fawcett Burton, Ottawa (CA); Shyamlal Ramchandani, Kingston (CA)

(73) Assignee: Analytics for Life, Ganaoque (CA)

( * ) Notice: Subject to any disclaimer, the term of this patent is extended or adjusted under 35 U.S.C. 154(b) by 206 days.

(21) Appl. No.: 14/295,615

(22) Filed: Jun. 4, 2014

Related U.S. Application Data (60) Provisional application No. 61/831,055, filed on Jun. 4, 2013.

(51) Int. Cl.
| | | |
|---|---|---|
| *A61B 5/0245* | (2006.01) | |
| *A61B 5/02* | (2006.01) | |
| *A61B 5/0452* | (2006.01) | |
| *A61B 5/00* | (2006.01) | |

(52) U.S. Cl.
CPC ........ *A61B 5/04525* (2013.01); *A61B 5/0452* (2013.01); *A61B 5/7264* (2013.01); *A61B 5/7275* (2013.01); *A61B 2576/023* (2013.01)

(58) Field of Classification Search
CPC .......... A61B 2576/023; A61B 5/04011; A61B 5/0452; A61B 5/7275; A61B 5/7264; A61B 5/04525

USPC .......................................................... 600/509
See application file for complete search history.

(56) References Cited

U.S. PATENT DOCUMENTS

| | | | |
|---|---|---|---|
| 2003/0083586 A1* | 5/2003 | Ferek-Petric | A61B 5/04011 600/512 |
| 2008/0114257 A1 | 5/2008 | Molin et al. | |
| 2010/0217144 A1* | 8/2010 | Brian | A61B 5/0452 600/523 |
| 2011/0251504 A1 | 10/2011 | Tereshchenko et al. | |

(Continued)

OTHER PUBLICATIONS

Bellenger, N.G., et al., "Comparison of left ventricular ejection fraction and volumes in hear failure by echocardiography, radionuclide ventriculography and cardiovascular magnetic resonance: Are they interchangeable?", European Heart Journal, vol. 21, No. 16, 2000, pp. 1387-1396.

(Continued)

*Primary Examiner* — Edward Moran
*Assistant Examiner* — Pamela M Bays
(74) *Attorney, Agent, or Firm* — Meunier Carlin & Curfman LLC (57) ABSTRACT

The present disclosure generally relates to systems and methods of a noninvasive technique for characterizing cardiac chamber size and cardiac mechanical function. A mathematical analysis of three-dimensional (3D) high resolution data may be used to estimate chamber size and cardiac mechanical function. For example, high-resolution mammalian signals are analyzed across multiple leads, as 3D orthogonal (X,Y,Z) or 10-channel data, for 30 to 800 seconds, to derive estimates of cardiac chamber size and cardiac mechanical function. Multiple mathematical approaches may be used to analyze the dynamical and geometrical properties of the data.

15 Claims, 5 Drawing Sheets

(56) References Cited

U.S. PATENT DOCUMENTS

| | | | |
|---|---|---|---|
| 2013/0096394 A1 | 4/2013 | Gupta et al. | |
| 2014/0194758 A1* | 7/2014 | Korenberg | A61B 5/04012 600/509 |
| 2014/0207005 A1* | 7/2014 | Bukkapatnam | A61B 5/7235 600/485 |

OTHER PUBLICATIONS

Edenbrandt, L., "Vectorcardiogram Synthesized From a 12-lead ECG: Superiority of the Inverse Dower Matrix," Journal of Electrocardiography, vol. 21, No. 4, 1988, pp. 361-367.

"Ejection Fraction" from Wikipedia. http://en.wikipedia.org/wiki/Ejection_fraction, last accessed Mar. 25, 2016, 5 pages.

Fioretti, P., et al., "Limitations of a QRS scoring system to assess left ventricular function and prognosis at hospital discharge after myocardial infarction," Br Heart J., vol. 53, No. 3, 1985, pp. 248-252.

Gholamrezanezhad, A., et al., "A correlative study comparing current different methods of calculating left ventricular ejection fraction," Nuclear Medicine Commun., vol. 28, No. 1, 2007, pp. 41-48.

Jaarsma, C., et al., "Comparison of Different Electrocardiographic Scoring Systems for Detection of any Previous Myocardial Infarction as Assessed With Cardiovascular Magnetic Resonance Imaging," American Journal of Cardiology, vol. 112, No. 8, 2013, pp. 1069-1074.

Mikell, F.L., et al., "Reliability of Q-wave formation and QRS score in predicting regional and global left ventricular performance in acute myocardial infarction with successful reperfusion," American Journal of Cardiology, vol. 57, No. 11, 1986, pp. 923-926.

Murkofsky, R.L., et al., "A Prolonged QRS Duration on Surface Electrocardiogram is a Specific Indicator of Left Ventricular Dysfunction," Journal of the American College of Cardiology, vol. 32, No. 2, 1998, pp. 476-482.

Nikitin, N.P., et al., "New generation 3-dimensional echocardiography for left ventricular volumetric and functional measurements: comparison with cardiac magnetic resonance," European Journal Echocardiography, vol. 7, No. 5, 2006, pp. 365-372.

Palmeri, S.T., et al., "A QRS scoring system for assessing left ventricular function after myocardial infarction," New England Journal of Medicine, vol. 306, No. 1, 1982, pp. 4-9.

Wagner, G.S., et al., "Evaluation of a QRS Scoring System for Estimating Myocardial Infarct Size. I. Specificity and Observer Agreement," Circulation, vol. 65, No. 2, 1982, pp. 342-347.

* cited by examiner

NONINVASIVE ELECTROCARDIOGRAPHIC METHOD FOR ESTIMATING MAMMALIAN CARDIAC CHAMBER SIZE AND MECHANICAL FUNCTION

CROSS-REFERENCE TO RELATED APPLICATION

The present application claims priority to U.S. Provisional Patent Application No. 61/831,055, filed Jun. 4, 2013, entitled "ESTIMATION OF LEFT VENTRICULAR (LV) EJECTION FRACTION (EF) BY MATHEMATICAL ANALYSIS OF HIGH-RESOLUTION ORTHOGONAL (X,Y,Z) ECG DATA," which is incorporated herein by reference in its entirety.

BACKGROUND

A variety of measures of cardiac function are used in clinical practice. The formulae used in their calculations are (1):

Stroke Volume (SV)=End Diastolic Volume (EDV)−
End Systolic Volume (ESV)

Ejection Fraction (EF)=(SV/EDV)×100%

Cardiac Output ($Q$)=SV×Heart Rate (HR)

Assessment of cardiac chamber size, including the left ventricle (LV), is commonly undertaken using cardiac ultrasound (echocardiography), radionuclide angiography (RNA), and cardiac magnetic resonance (CMR) imaging. Each technique measures the change in chamber size with each heartbeat, reflecting the amount of blood ejected with each heartbeat. These measures are then used to estimate cardiac mechanical function. The SV is the fraction of blood ejected with each heartbeat and EF is that fraction divided by the amount of blood at rest or in diastole, as measured using the end diastolic volume (EDV). Cardiac output (Q) reflects the volume of blood over time and is the product of SV multiplied by heart rate (HR).

Presently used techniques, to estimate Left Ventricular Ejection Fraction (LVEF), are costly, have limited access in many regions, and require interpretation by a clinician. Moreover, techniques that use radionuclide pharmaceutics pose a risk to patients and healthcare providers in terms of radiation exposure. Further, there is generally poor correlation between these techniques in terms of the LVEF value obtained. Of the various techniques used, both CMR and RNA are considered to represent the "gold standard" methods for assessing LVEF in terms of the value obtained and for prognosis. Studies comparing techniques considered to provide the most reliable LVEF estimates, RNA with CMR, typically show correlation values in a modest to high range (r>0.7). Further, with these gold standard techniques a 10% or larger individual difference in LVEF is found in 23% of patients. A technology that can reliably estimate LVEF from a common cardiovascular test that is noninvasive and can be readily implemented (i.e., an ECG) has tremendous clinician potential.

Algorithms commonly employed in signal processing of cardiac signals are typically rudimentary. They can be improved upon using contemporary techniques that evaluate the detailed characteristics of high-resolution 3D ECG signals in terms of geometric relationships, conduction properties, and other characteristics.

The surface ECG contains detailed information of the electrical properties of the heart. A surface ECG signal represents the summation of the individual action-potentials from each, and every, cardiac cell in syncytium. Hence, global alterations in the surface ECG would be expected to reflect the mechanical function of the heart. Moreover, information related to the conduction properties of myocardial tissue is inherent in the surface ECG. A major challenge is the discrimination of pertinent information from a long quasi-periodic ECG signal while excluding noise contamination.

There is a distinct lack of ECG-based algorithms to estimate cardiac chamber size and cardiac mechanical function. Various metrics have been developed to estimate chamber enlargement and cardiac mechanical function. These include i) estimating chamber size based on the amplitude and duration of ECG features (e.g., left atrial abnormality) and ii) estimating cardiac mechanical function based on the presence or absence of Q waves, the presence or absence of prominent conduction delays, and the overall amplitude of ECG signals (e.g., QRS voltage). While each approach appeared promising during the development phase, none has been shown to be useful with independent validation in less selected populations (3-10). Yet, it is desirable for an ECG-based system and method to determine cardiac chamber size and systolic function (i.e., LVEF) due to the utility of this data in screening and for daily clinical decision-making. Moreover, these data have been shown to have important prognostic value.

SUMMARY OF THE DISCLOSURE

The present disclosure generally relates to a noninvasive electrocardiographic (ECG) method and technique for characterizing cardiac chamber size and cardiac mechanical function. Disclosed herein are methods that utilize mathematical analysis of three-dimensional (3D) high resolution ECG data to estimate chamber size and cardiac mechanical function. For example, high-resolution mammalian ECG signals are analyzed across multiple leads, as 3D orthogonal (X,Y,Z) or 10-channel data for 30 to 800 seconds to derive estimates of cardiac chamber size and cardiac mechanical function. Multiple mathematical approaches may be used to analyze the dynamical and geometrical properties of the ECG data understudy.

In accordance with an aspect of the disclosure, there is a disclosed a noninvasive method for analyzing mammalian ECG signals to accurately estimate cardiac chamber size and cardiac mechanical function. The method includes obtaining 3D ECG data; processing the ECG data to noninvasively determine a cardiac chamber size; processing the ECG data to noninvasively estimate cardiac mechanical function; applying a model to measure at least one of a sum QRST integral, 3D ECG volume integral, spatial QRST angle, QRS loop volumes, T loop volumes, spatial ventricular gradient, spatial ventricular gradient azimuth, spatial ventricular gradient elevation and beat-to-beat variability in such values; and adjusting results of the model with clinical data to estimate cardiac chamber size and cardiac chamber mechanical function.

In accordance with other aspects, there is provided an ECG analysis system for analyzing ECG measurements obtained from a patient to determine a patient's cardiac chamber size and cardiac mechanical function corresponding to a level of risk of the patient experiencing a subsequent clinical event. The ECG analysis system may include a 3D ECG measuring component that obtains orthogonal or multi-lead ECG measurements and an ECG analysis component operatively connected to the ECG measuring component that receives the ECG measurements, performs an ECG analysis, and provides ECG analysis results in a user-readable format. The ECG analysis includes determining at least one cardiac event risk factor having a value, the at least one cardiac event risk factor being determinable from a group of cardiac function values, cardiac output, stroke volume, end-diastolic volume, end-systolic volume and ejection fraction, and beat-to-beat variability in such values.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

The present disclosure has been designed to assess cardiac chamber size and cardiac mechanical function by evaluating the electrical activity of the heart. With reference to the equations that follow the written description below, the present disclosure provides a method whereby high-resolution mammalian ECG signals are analyzed across multiple leads, as 3D orthogonal (X,Y,Z) or 10-channel data, for 30 to 800 seconds (Eq. 1), to derive estimates of cardiac chamber size and cardiac mechanical function. Multiple mathematical approaches are used to analyze the dynamical and geometrical properties of the ECG data under study.

Figure 1:
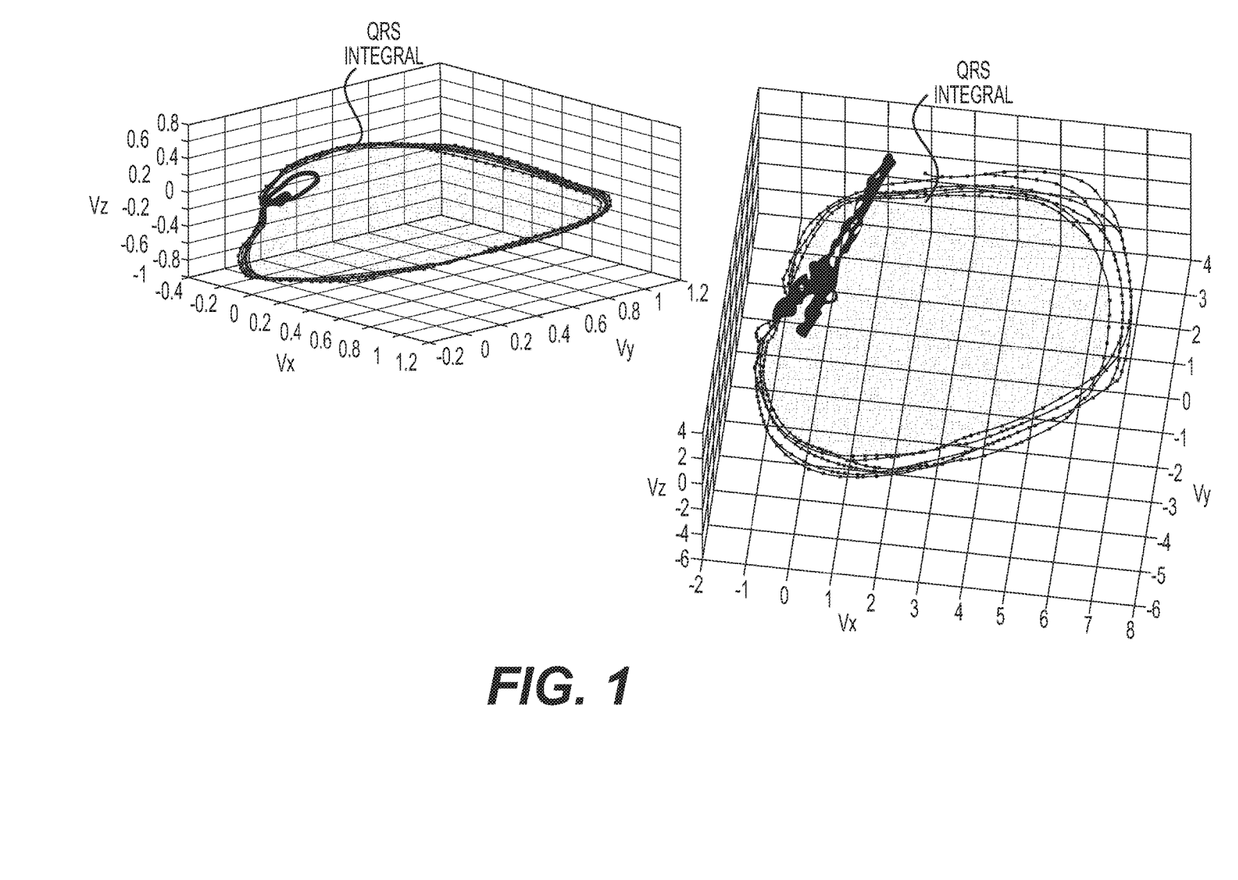
FIG. 1 illustrates exemplar vectorcardiograms and three dimensional integrals that may be computed and used in estimating cardiac chamber size and mechanical function.

FIG. 1 illustrates exemplar vectorcardiograms and three dimensional integrals that may be computed and used in estimating cardiac chamber size and mechanical function. The first method uses vectorcardiography and topology to characterize the ECG manifestations of the cardiac repolarization and depolarization process. The vectorcardiogram (VCG) is a method that records, in the three planes of space, the electrical potential of the heart during the cardiac cycle. Chamber activation manifests as the P loop (atrial depolarization), a dominant high amplitude QRS loop (ventricular depolarization), and the T loop (ventricular depolarization (Eq. 10), which result from the spatial temporal summation of multiple vectors of bioelectric potentials that originate in the heart during the cardiac cycle. The entirety of the cycle is known as the PQRST, and can be referenced in sub-cycles. The spatial electrical gradients (Eq. 4) embedded in the electrical properties relate to the volume and the local properties of the chamber of interest. This includes bioelectric inhomogeneities and the physics of cardiac mechanical function.

Figure 2:
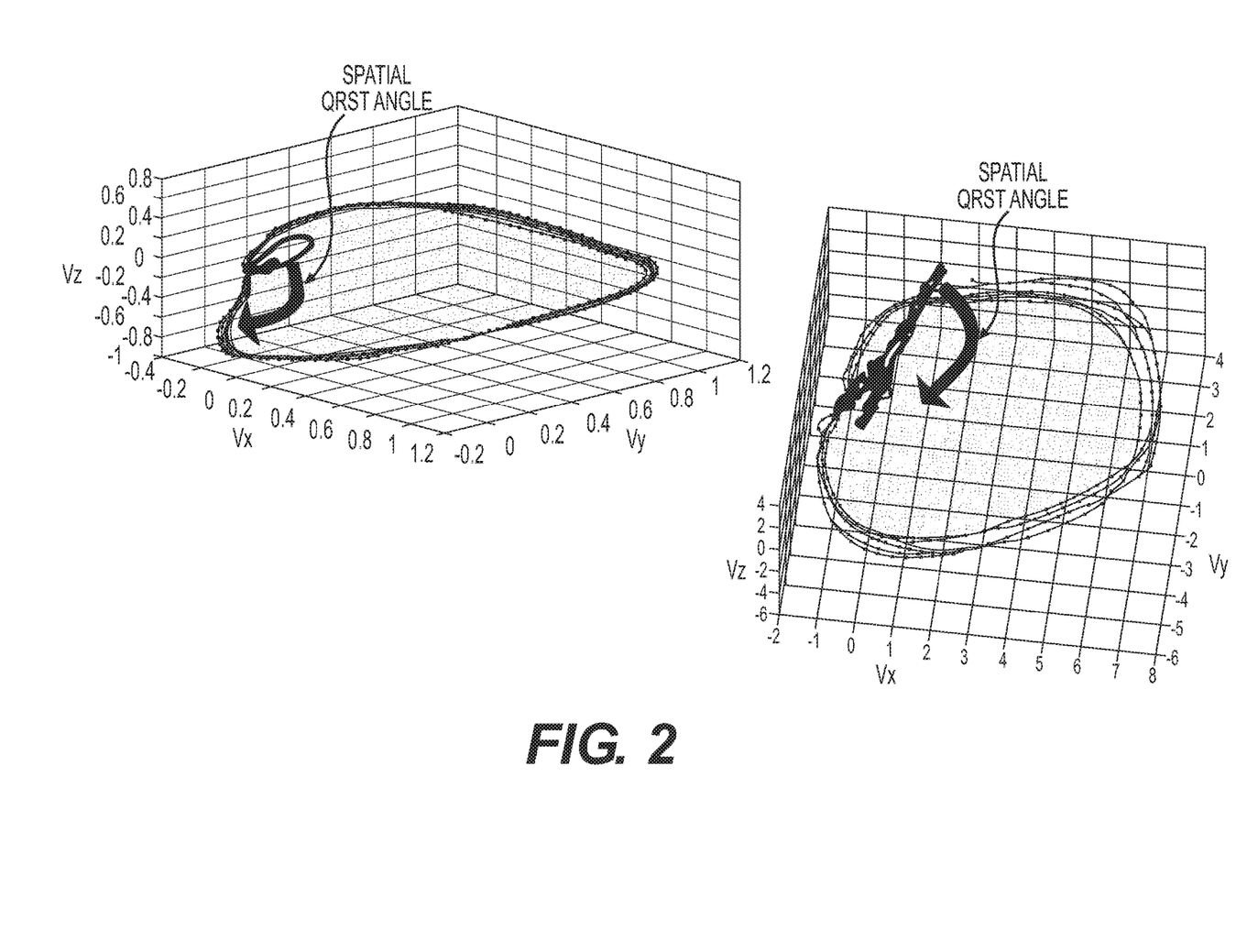
FIG. 2 illustrates, in the vectorcardiograms of FIG. 1, a spatial QRST angle that may be used as a metric for evaluating cardiac chamber size and mechanical function.

FIG. 2 illustrates a spatial QRST angle that may be used as a metric for evaluating cardiac chamber size and mechanical function. The spatial gradients obtained by the VCG can be measured in a variety of ways including the QRST integral (Eq. 2), which captures the peak amplitudes, the size of the QRS vector loop (Eq. 9), and the angles of depolarization and repolarization (Eqs. 5,6). The depolarization of the heart moves from the endocardium to the epicardium, and this is captured in the QRS vector loop volume (Eq. 9) morphology. This rapid myocardial activation, in early ventricular systole, develops perfusion pressure. Maximal right and left pressure is reached before the beginning of the T wave. These pressure gradients embed cardiac function information in the voltage spatial gradients (Eq. 4). The pressure in the endocardium is higher than in the epicardium; this forces ventricular myocytes to repolarize in the epicardium first. The unequal distribution of endocardial pressure throughout the ventricles delays the time the endocardium begins to repolarize and this delay is correlated to cardiac output. These delays can be quantified with the volume QRST integral (Eq. 3) over an ECG signal across each of the three leads (X, Y, Z) in a given time period (typically 30-800 seconds). The magnitude of this integral is predictive when extracting LV chamber size and estimating LVEF from the ECG.

Other features required to reliably assess LVEF include, but are not limited to, the morphology of the VCG loop, conduction velocity over the initial 50% of the QRS VCG (Eq. 7), and spatial alterations in the QRST angle.

Corrections for body size (body mass index), gender, cardioactive medications, and variations in ECG lead placement are required to reliably assess LVEF.

The aforementioned techniques and approaches can also be used to assess the size and function of other chambers, including the right and left atria, and to quantify myocardial relaxation, commonly referred to as diastolic function.

Figure 3:
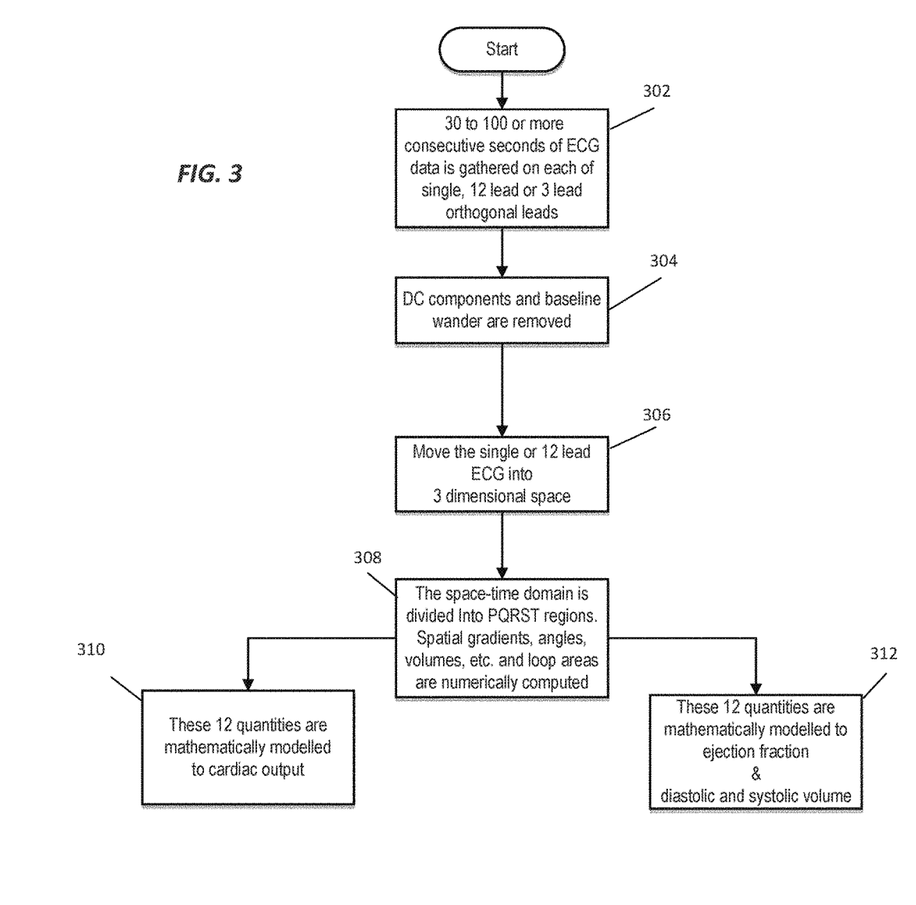
FIG. 3 illustrates a workflow to generate a model that is predictive of ejection fraction, diastolic volume, systolic volume, cardiac chamber volumes and masses.

FIG. 3 illustrates a workflow to generate a model that is predictive of ejection fraction, diastolic volume, systolic volume, cardiac chamber volumes and mass. This includes left ventricular (LV) and right ventricular (RV) end-systolic (ES) and end-diastolic (ED) linear dimensions and volumes; LV and RV ejection fraction (EF), and LV mass (LVM); and left atrial (LA) and right atrial (RA) end-systolic volumes.

At 302, 30 to 100 (or more) consecutive seconds of ECG data are gathered at each of a single, 12-lead, or 3-lead, orthogonal lead(s). At 304, DC components and baseline wander are removed. This may be performed by using a modified moving average filter created for each lead. At 306, the single or 12-lead ECG data is moved into three-dimensional space. This may be performed, for example, using delayed phase space reconstruction or techniques using the Inverse Dower matrix (11). At 308, the space-time domain is divided into PQRST regions, and spatial gradients, angles, volumes, etc., and loop areas are numerically computed. At 310, 12 quantities are mathematically modelled to cardiac output. Alternatively or additionally, at 312, the 12 quantities are mathematically modelled to ejection fraction, and diastolic and systolic volume. Thus, the workflow of FIG. 3 provides a method to model cardiac output, ejection fraction, and diastolic and systolic volume.

Figure 4:
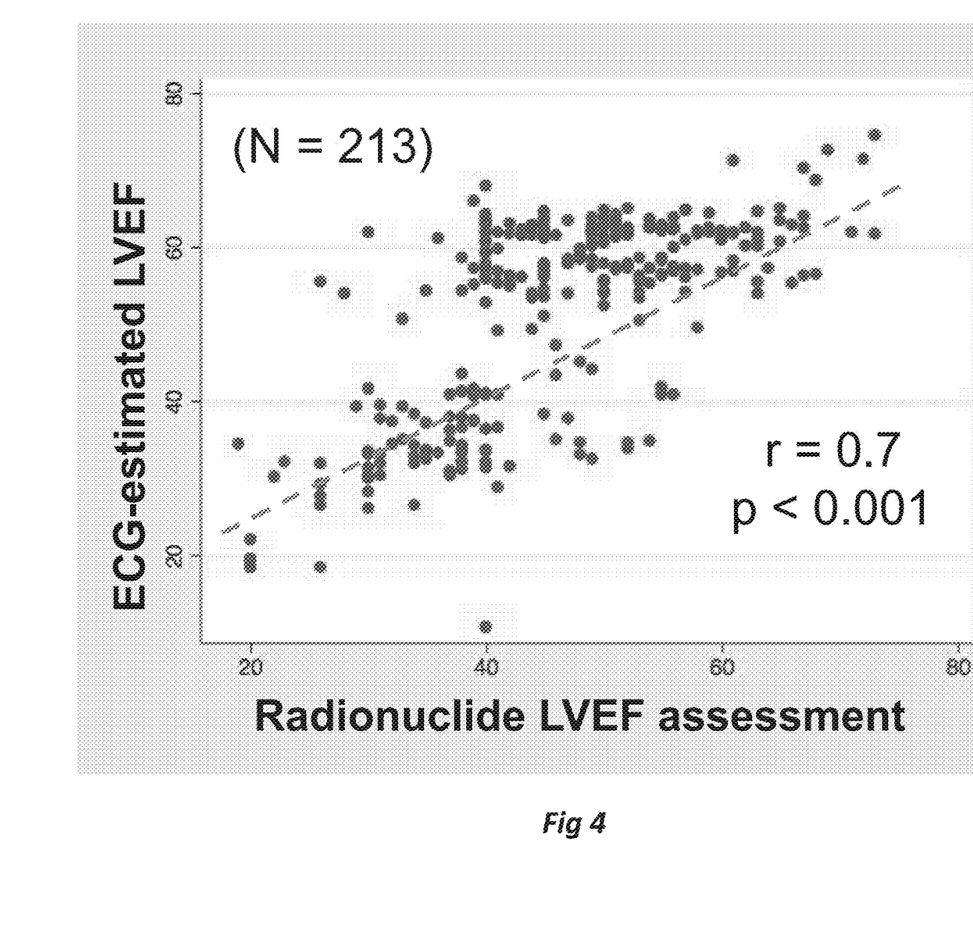
FIG. 4 illustrates a correlation plot of predicted LVEF from the ECG against the MUGA measured ejection fraction.

FIG. 4 is a correlation plot of predicted LVEF from the ECG of the present disclosure against the MUGA-measured ejection fraction (multiple gated acquisition measured ejection fraction are also referred to as radionuclide angiography LV ejection fraction). The techniques described herein were applied to a dataset of 213 orthogonal high-resolution (1000 Hz) ECGs (ECG-EF) with paired MUGA-evaluated left ventricular ejection fraction values. A statistically significant linear correlation in LVEF values was found ($r=0.7$, p<0.001). 3D-High Resolution ECG-computed LVEF and MUGA-measured LVEF had similar prognostic utility. For each 10% increase in LVEF, the risk of death was 40% lower with the MUGA (p<0.01) and 54% lower with ECG-estimated (p<0.01) LVEF.

Figure 5:
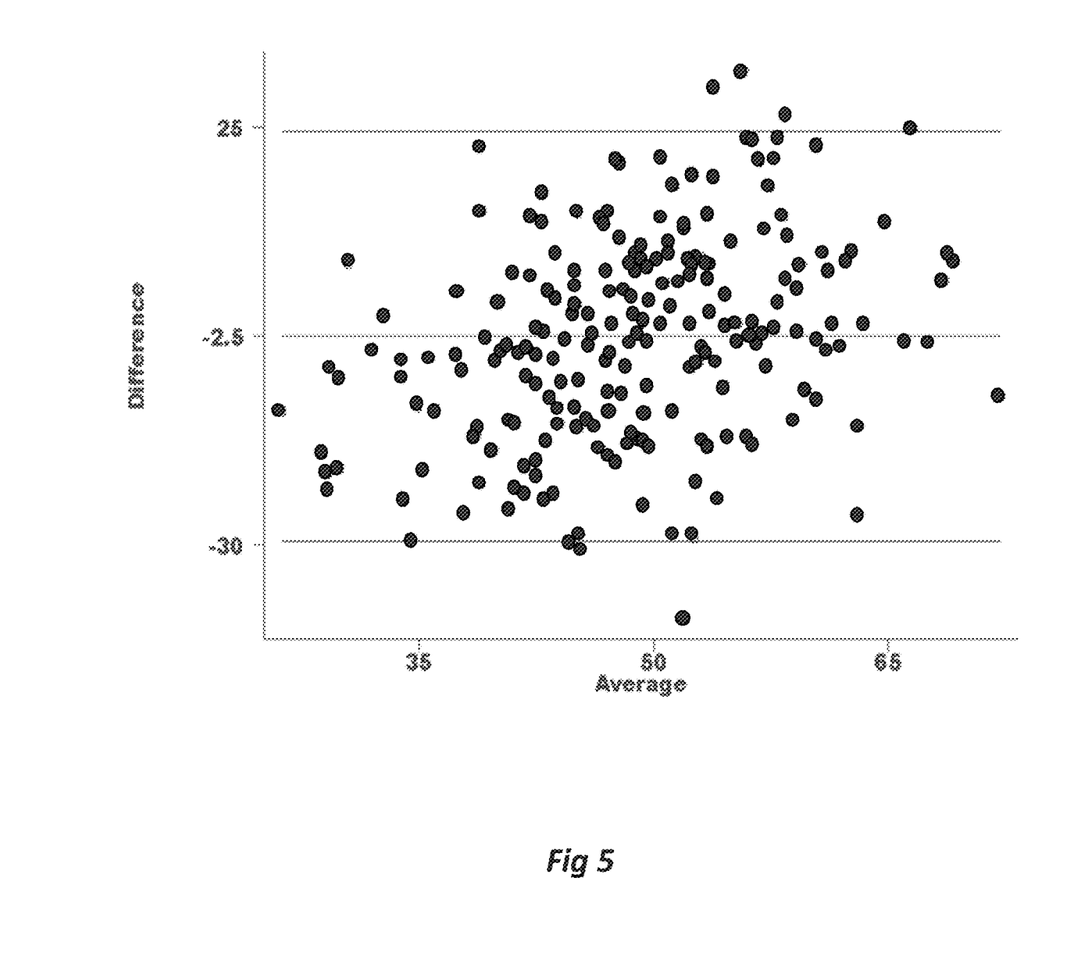
FIG. 5 illustrates a Bland-Altman plot of predicted LVEF from an ECG-measured assessment and a MUGA-measured assessment.

FIG. 5 is a Bland-Altman plot used here to examine the disparity between the two measurements (ECG-EF vs MUGA EF) described and shown in connection with FIG. 4. The mean ECG-estimated LVEF was, on average, 2.5% (95% confidence interval 0.7% to 4.3%) lower than the MUGA-estimated LVEF. The range of the MUGA-calculated ejection fraction values was 15% to 75%. Together, the results described by FIGS. 4 and 5 demonstrate that the LVEF computed from the ECG signal using the methods, disclosed is clinically equivalent to that measured by the gold standard method of MUGA. The equation that combined the different characterization methods discussed to create these results, is below. This exemplar is not limiting and there are other solutions in this family with similar diagnostic ability, two of which are also provided.

Ejection Fraction Exemplar One=spatial VentricularGradientAzimuth+TWaveLoopVolume^2+ 36.63895238712*erf(1.29854235984933+ spatialVentricularGradientAzimuth*QRVelocity−TWaveLoopVolume)+(3.73595220608718* spatialConductionVelocityGradient− 4.95485967820254*spatialVentricularGradientElevation)/(TWaveLoop Volume^2+erf(spatialVentricularGradient^4/ (3.73595220608718*spatialConductionVelocity Gradient−4.95485967820254*spatialVentricularGradientElevation)))+CF Ejection Fraction Exemplar Two=−0.381568077439472/ (spatialVentricularGradientElevation*erf(spatialVentricularGradientAzimuth))+41.2156652358613*gauss (gauss(6.56930578402457+−2/ spatialVentricularGradientAzimuth))+ 0.930158852689193* spatialConductionVelocityGradient^2*erfc(erf(spatial-VentricularGradient))/(spatialVentricularGradientElevation* TWaveLoopVolume)+CF Ejection Fraction Exemplar Three=17.3495543240011+ 1.25836680957487*spatialConductionVelocityGradient+0.380736486799911/spatialVentricularGradient+ 0.310999364860442*spatialVentricularGradient-Elevation*spatialVentricularGradientAzimuth*erf (gauss(−2)*xyQRSLoopArea)+ 0.310999364860442*spatialVentricular-GradientElevation*TWaveLoop Volume^2*erf (gauss(−2)*xyQRSLoopArea)+ 29.6734283926203*gauss(6.707623776*spatialVentricularGradient* spatialVentricularGradientElevation+− 6.746230385*spatialVentricularGradientAzimuth* spatialVentricularGradientElevation^3/spatialVentricularGradient)+11.394690922442*spatialVentricularGradientElevation*erf(gauss(−2)*xyQRSLoopArea)* erf(1.29854236+ spatialVentricularGradientAzimuth*QRVelocity−TWaveLoopVolume)+0.310999364860442* spatialVentricularGradientAzimuth*erf(gauss(−2)*xy-QRSLoopArea)*erf(2258*PQRSTIntegralProd/ yzQRSLoopArea)*gauss(spatialVentricularGradient^5/ (erf(spatialVentricularGradientAzimuth^2)*erf (2258*PQRSTIntegralProd/yzQRSLoopArea)))+ 0.310999364860442*TWaveLoopVolume^2*erf(gauss (−2)*xyQRSLoopArea)*erf (2258*PQRSTIntegralProd/yzQRSLoopArea)*gauss (spatialVentricularGradient^5/(erf (spatialVentricularGradientAzimuth^2)*erf (2258*PQRSTIntegralProd/yzQRSLoopArea)))+ (230.0195707867421*spatialVentricularGradient* TWaveLoopVolume*spatialConduction-VelocityGradient−30.5300327217556* spatialVentricularGradient*spatialVentricular-GradientElevation*TWaveLoopVolume)/ (xzQRSLoopArea*TWaveLoopVolume^2+ xzQRSLoopArea*erf(spatialVentricularGradient^4/ (30.735952206*spatialConductionVelocityGradient− 4.954859678*spatialVentricularGradientElevation)))+ 11.394690922442*erf(gauss(−2)*xyQRSLoopArea)* erf(2258*PQRSTIntegralProd/yzQRSLoopArea)*erf (1.29854236+ spatialVentricularGradientAzimuth*QRVelocity−TWaveLoopVolume)*gauss (spatialVentricularGradient^5/(erf (spatialVentricularGradientAzimuth^2)*erf (2258*PQRSTIntegralProd/yzQRSLoopArea)))+ 1.16187876321497*spatialVentricularGradient-Elevation*spatialConductionVelocityGradient*erf (gauss(−2)*xyQRSLoopArea)*erf(2258*PQRSTIntegralProd/yzQRSLoopArea)*gauss(spatial-VentricularGradient^5/(erf (spatialVentricularGradientAzimuth^2)*erf (2258*PQRSTIntegralProd/yzQRSLoopArea)))/(spatialVentricularGradientElevation* TWaveLoopVolume^2+ spatialVentricularGradientElevation*erf(spatialVentricularGradient^4/(3.735952206*spatialConduction-VelocityGradient− 4.954859678*spatialVentricularGradientElevation)))+ (6.16163417448763*spatialVentricularGradient* spatialVentricularGradientAzimuth*TWaveLoop-Volume+25.6981797*TWaveLoopVolume* spatialVentricularGradient^2+6.16163417448763* spatialVentricularGradient*TWaveLoopVolume* TWaveLoopVolume^2+1.863894357* TWaveLoopVolume*spatialConductionVelocity-Gradient*spatialVentricularGradient^2+ 225.755821163649*spatialVentricularGradient* TWaveLoopVolume*erf(1.29854236+ spatialVentricularGradientAzimuth*QRVelocity−TWaveLoopVolume)+43.95231606* TWaveLoopVolume*spatialVentricularGradient^2* gauss(6.707623776*spatialVentricularGradient*spatial VentricularGradientElevation+−6.746230385* spatialVentricularGradientAzimuth*spatial-VentricularGradientElevation^3/spatialVentricularGradient))/xzQRSLoopArea+(1.16187876321497* spatialVentricularGradientElevation* spatialConductionVelocityGradient*erf(gauss(−2)*xy-QRSLoopArea)−1.54095821283061* spatialVentricularGradientElevation^2* erf(gauss(−2)*xyQRSLoopArea)− 1.54095821283061*spatialVentricular-GradientElevation*erf(gauss(−2)*xyQRSLoopArea)* erf(2258*PQRSTIntegralProd/yzQRSLoopArea)* gauss(spatialVentricularGradient^5/(erf (spatialVentricularGradient^zimuth^2)*erf (2258*PQRSTIntegralProd/yzQRSLoopArea))))/ (TWaveLoopVolume^2+erf (spatialVentricularGradient^4/ (3.735952206*spatialConductionVelocityGradient− 4.954859678*spatialVentricularGradientElevation)))− spatialVentricularGradientElevation* TWaveLoopVolume*spatialConduction-VelocityGradient+CF As described herein, the following example formulae, equations and relationships may be used to estimate LVEF:
1. ECG time window=t2−t1
2. SumQRST=$\int_{t1}^{t2}|Vx|+\int_{t1}^{t2}|Vy|+\int_{t1}^{t2}|Vz|$
3. DECG Volume Integral=VPQRST=$\int_{t1}^{t2}|Vx|*\int_{t1}^{t2}|Vy|*\int_{t2}^{t1}|Vz|$
4. Spatial ventricular gradient (SVG)

$$= \sqrt{\left(\left(\int_{t1}^{t2}Vx\right)^2 + \left(\int_{t1}^{t2}Vy\right)^2 + \left(\int_{t1}^{t2}Vz\right)^2\right)}$$

5. Spatial ventricular gradient elevation=arccos($(\int_{t1}^{t2}Vy\,dt)/SVG$)
6. Spatial ventricular gradient azimuth=arctan($(\int_{t1}^{t2}Vzdt)/\int_{t1}^{t2}Vxdt$)
7. Spatial conduction velocity gradient (SCVG)= $\sqrt{((dVx/dt)^2+(dVy/dt)^2+(dVz/dt)^2)}$
8.

$$\text{Spatial conduction velocity elevation} = \arccos\left(\frac{\frac{dV_y}{dt}}{SCVG}\right)$$

9. 3DQRS loop volume=SumQRS=$\int_{t1}^{t2}|Vx|*\int_{t1}^{t2}|Vy|*\int_{t1}^{t2}|Vz|$
10. 3DT loop volume=VT=$\int_{t1}^{t2}|Vx|*\int_{t1}^{t2}|Vy|*\int_{t1}^{t2}|Vz|$
11. Cardiac output=f(3DT loop volume, 3DQRS loop volume, Spatial ventricular gradient, 3DECG Volume Integral, SumQRST)
12. Stroke volume=f(3DECG Volume Integral, 3DT loop volume, 3DQRS loop volume, SumQRST, peak spatial QRST angle)
13. End-systolic volume=f(3DECG Volume Integral, 3DT loop volume, 3DQRS loop volume, SumQRST, peak spatial QRST angle, Spatial ventricular gradient elevation)
14. End-diastolic volume=f(3DECG Volume Integral, 3DT loop volume, 3DQRS loop volume, SumQRST, peak spatial QRST angle, Spatial ventricular gradient elevation)
15. CF=Correction factors which include race, weight, age, gender, medication
16.

$$\text{Ejection Franction} = \frac{\text{End diastolic volume} - \text{End systolic volume}}{\text{End diastolic volume}} * 100$$

Having thus described implementations of the claimed invention, it will be rather apparent to those skilled in the art that the foregoing detailed disclosure is intended to be presented by way of example only, and is not limiting. Many advantages for non-invasive method and system for estimate cardiac chamber size and cardiac mechanical function have been discussed herein. Various alterations, improvements, and modifications will occur and are intended to those skilled in the art, though not expressly stated herein. Any alterations, improvements, and modifications are intended to be suggested hereby, and are within the spirit and the scope of the claimed invention. Additionally, the recited order of the processing elements or sequences, or the use of numbers, letters, or other designations therefore, is not intended to limit the claimed processes to any order except as may be specified in the claims. Accordingly, the claimed invention is limited only by the following claims and equivalents thereto.

REFERENCES

1. "Ejection Fraction" from Wikipedia. http://en.wikipedia.org/wiki/Ejection_fraction. Last accessed Jun. 3, 2014.
2. Jaarsma C, Bekkers S C, Haidari Z, et al. Comparison of Different Electrocardiographic Scoring Systems for Detection of any Previous Myocardial Infarction as Assessed With Cardiovascular Magnetic Resonance Imaging. Am J Cardiol. 2013 Jul. 2. pii: S0002-9149(13) 01273-3.
3. Gholamrezanezhad A, Mirpour S, Esfehani A F, et al. A correlative study comparing current different methods of calculating left ventricular ejection fraction. Nucl Med Commun. 2007; 28(1):41-8.
4. Bellenger N G, Burgess M I, Ray S G, et al. Comparison of left ventricular ejection fraction and volumes in heart failure by echocardiography, radionuclide ventriculography and cardiovascular magnetic resonance; are they interchangeable? Eur Heart J. 2000; 21(16):1387-96.
5. Nikitin N P, Constantin C, Loh P H, et al. New generation 3-dimensional echocardiography for left ventricular volumetric and functional measurements: comparison with cardiac magnetic resonance. Eur J Echocardiogr. 2006; 7(5):365-72.
6. Palmeri S T, Harrison D G, Cobb F R, et al. A QRS scoring system for assessing left ventricular function after myocardial infarction. N Engl J Med. 1982; 306(1):4-9.
7. Wagner G S, Freye C J, Palmeri S T, et al. Evaluation of a QRS scoring system for estimating myocardial infarct size. I. Specificity and observer agreement. Circulation. 1982; 65(2):342-7.
8. Mikell F L, Petrovich J, Snyder M C, Reliability of Q-wave formation and QRS score in predicting regional and global left ventricular performance in acute myocardial infarction with successful reperfusion. Am J Cardiol. 1986; 57(11):923-6.
9. Fioretti P, Brower R W, Lazzeroni E, et al. Limitations of a QRS scoring system to assess left ventricular function and prognosis at hospital discharge after myocardial infarction. Br Heart J. 1985; 53(3):248-52.
10. Murkofsky R L, Dangas G, Diamond J A, et al. A prolonged QRS duration on surface electrocardiogram is a specific indicator of left ventricular dysfunction. J Am Coll Cardiol. 1998; 32(2):476-82.
11. Edenbrandt L, Pahlm O. Vectorcardiogram Synthesized From a 12-lead ECG: Superiority of the Inverse Dower Matrix. Journal of Electrocardiography 1988; 21(4): 361-367.

All references, including publications, patent applications, and patents, cited herein are hereby incorporated by reference to the same extent as if each reference was individually and specifically indicated to be incorporated by reference and were set forth in its entirety herein.

What is claimed is:
1. A method to noninvasively estimate cardiac chamber size and cardiac mechanical function, including left ventricular ejection fraction, the method comprising:
obtaining, by a processor, three-dimensional (3D) orthogonal data from a measurement of one more surface electrical signals of a subject, wherein the three-dimensional (3D) orthogonal data is derived from measurements acquired via noninvasive equipment configured to measure electrical properties of the heart;

determining, by the processor, via a numerical integral operation of one or more vectorcardiogram components associated with a vectorcardiogram of the 3D orthogonal data, i) one or more first parameters selected from the group consisting of a sum QRST integral parameter, a 3D volume integral parameter, a spatial QRST angle parameter, a 3D QRS loop volume parameter, a 3D T-loop volume parameter, a spatial ventricular gradient parameter, a spatial ventricular gradient azimuth parameter, a spatial ventricular gradient elevation parameter, and ii) one or more second parameters associated with beat-to-beat variability of the one or more first parameters; and determining, by the processor, an estimate cardiac chamber size parameter by applying the one or more first parameters and the one or more second parameters in one or more first models associated with the cardiac chamber size; and determining, by the processor, one or more cardiac chamber mechanical function parameters by applying the one or more first parameters and the one or more second parameters in one or more second models associated with each cardiac chamber mechanical functions; and cause, by the processor, the estimate cardiac chamber size parameter and the one or more cardiac chamber mechanical function parameters to be presented in a graphical user interface.

2. The method of claim 1, wherein the vectorcardiogram comprises a 12- or N-dimensional phase space transformation of the 3D orthogonal data.

3. The method of claim 1, wherein the 3D orthogonal data is obtained via an ECG measurement equipment that includes a surface ECG instrument.

4. The method of claim 3, wherein the 3D orthogonal data is obtained via the ECG measurement equipment over a time period of about 30 seconds to about 800 seconds.

5. The method of claim 1, wherein the one or more cardiac chamber mechanical function parameters are selected from the group consisting of a cardiac output parameter, a stroke volume parameter, an end-diastolic volume parameter, an end-systolic volume parameter, and an ejection fraction parameter.

6. The method of claim 1, wherein the presented one or more cardiac chamber mechanical function parameters are subsequently used to screen patients for structural heart disease.

7. The method of claim 1, wherein the determined one or more cardiac chamber mechanical function parameters comprise ventricular mechanical cardiac function values, the method further comprising using a variability of the ventricular mechanical cardiac function values among a plurality of heart beats in the 3D orthogonal data to determine presence of a decline in cardiac function to assess risk of clinical events.

8. The method of claim 7, wherein the ventricular mechanical cardiac function values include cardiac output, stroke volume, end-diastolic volume, end-systolic volume and ejection fraction.

9. The method of claim 1, wherein the determined one or more cardiac chamber mechanical function parameters comprise atrial mechanical cardiac function values, the method further comprising using a variability of the atrial mechanical cardiac function values among a plurality of heart beats in the 3D orthogonal data to determine presence of a reduced atrial cardiac function and to assess risk of clinical events.

10. The method of claim 1, wherein the Sum QRST integral parameter is determined by:

$$\int_{t_1}^{t_2} |V_x| + \int_{t_1}^{t_2} |V_y| + \int_{t_1}^{t_2} |V_z|$$

wherein $V_x$, $V_y$, and $V_z$ are the one or more vectorcardiogram components, and wherein $t_2-t_1$ comprises a measurement time window for the 3D orthogonal data.

11. The method of claim 1, wherein the 3D QRS loop volume parameter, the 3D T-loop volume parameter, and the 3D volume integral parameter are determined by:

$$\int_{t_1}^{t_2} |V_x| * \int_{t_1}^{t_2} |V_y| * \int_{t_1}^{t_2} |V_z|$$

wherein $V_x$, $V_y$, and $V_z$ are the one or more vectorcardiogram components, and wherein $t_2-t_1$ comprises a measurement time window for the 3D orthogonal data.

12. The method of claim 1, wherein the spatial ventricular gradient (SVG) parameter is determined by:

$$\sqrt{\left(\int_{t_1}^{t_2} V_x\right)^2 + \left(\int_{t_1}^{t_2} V_y\right)^2 + \left(\int_{t_1}^{t_2} V_z\right)^2}$$

wherein $V_x$, $V_y$, and $V_z$ are the one or more vectorcardiogram components, and wherein $t_2-t_1$ comprises a measurement time window for the 3D orthogonal data.

13. The method of claim 1, wherein the spatial ventricular gradient azimuth parameter is determined by:

$$\arctan \frac{\int_{t_1}^{t_2} V_z}{\int_{t_1}^{t_2} V_x \, dt}$$

wherein $V_x$ and $V_z$ are the one or more vectorcardiogram components, and wherein $t_2-t_1$ comprises a measurement time window for the 3D orthogonal data.

14. The method of claim 1, wherein the spatial ventricular gradient elevation parameter is determined by:

$$\arccos \frac{\int_{t_1}^{t_2} V_y}{\sqrt{\left(\int_{t_1}^{t_2} V_x\right)^2 + \left(\int_{t_1}^{t_2} V_y\right)^2 + \left(\int_{t_1}^{t_2} V_z\right)^2}}$$

wherein $V_x$, $V_y$, and $V_z$ are the one or more vectorcardiogram components, and wherein $t_2-t_1$ comprises a measurement time window for the 3D orthogonal data.

15. The method of claim 1, wherein the one or more first parameters comprise spatial gradient parameters, including a peak amplitude of the vectorcardiogram, a size of a QRS vector loop of the vectorcardiogram, an angle of depolarization, an angle of repolarization, and a voltage spatial gradient.

* * * * *